US012582830B2

(12) United States Patent
Arvanian et al.

(10) Patent No.: US 12,582,830 B2
(45) Date of Patent: Mar. 24, 2026

(54) DEVICES, SYSTEMS AND METHODS FOR TREATING BACK PAIN WITH EMS

(71) Applicant: UNITED STATES GOVERNMENT AS REPRESENTED BY THE DEPARTMENT OF VETERANS AFFAIRS, Washington, DC (US)

(72) Inventors: Victor Arvanian, Northpoint, NY (US); Hayk Petrosyan, Northpoint, NY (US); Magda Fahmy, Northpoint, NY (US); Asrat Tesfa, Northpoint, NY (US); Joseph Fasano, Northpoint, NY (US)

(73) Assignee: United States Government as Represented by the Department of Veterans Affairs, Washington, DC (US)

( * ) Notice: Subject to any disclaimer, the term of this patent is extended or adjusted under 35 U.S.C. 154(b) by 1072 days.

(21) Appl. No.: 17/636,627

(22) PCT Filed: Aug. 21, 2020

(86) PCT No.: PCT/US2020/047337
§ 371 (c)(1),
(2) Date: Feb. 18, 2022

(87) PCT Pub. No.: WO2021/041187
PCT Pub. Date: Mar. 4, 2021

(65) Prior Publication Data
US 2022/0339457 A1      Oct. 27, 2022

Related U.S. Application Data

(60) Provisional application No. 62/891,012, filed on Aug. 23, 2019.

(51) Int. Cl.
A61N 2/00       (2006.01)
A61N 2/02       (2006.01)

(52) U.S. Cl.
CPC ............. *A61N 2/008* (2013.01); *A61N 2/006* (2013.01); *A61N 2/02* (2013.01)

(58) Field of Classification Search
CPC .......... A61N 2/00; A61N 2/002; A61N 2/004; A61N 2/006; A61N 2/008; A61N 2/02
See application file for complete search history.

(56) References Cited

U.S. PATENT DOCUMENTS 6,042,531 A   *   3/2000   Holcomb .................. A61N 2/00
                                                        600/15
10,245,439 B1 *   4/2019   Schwarz ................ A61N 2/006
                                (Continued)

FOREIGN PATENT DOCUMENTS

CN        102802725    * 11/2012   .............. A61N 2/02
DE        202018106565 * 10/2019   .............. A61N 2/02
GB        2303066      * 2/1997    .............. A61N 2/02

*Primary Examiner* — Carrie R Dorna
(74) *Attorney, Agent, or Firm* — Ballard Spahr LLP

(57)      ABSTRACT

Devices, systems, and methods for treating lower back pain (e.g., chronic lower back pain) with electromagnetic stimulation are disclosed. A device for treating lower back pain can have a seat portion, a backrest portion, and an electromagnetic stimulation coil operatively associated with the backrest portion. The electromagnetic stimulation coil can be positioned to apply electromagnetic stimulation to a spine of a patient while the patient is seated on the seat portion.

15 Claims, 12 Drawing Sheets

(56) References Cited

U.S. PATENT DOCUMENTS

2008/0262287 A1* 10/2008 Dussau ................... A61N 2/02
                                                        600/13
2013/0090515 A1*  4/2013 Chang ..................... A61N 2/06
                                                         600/9

* cited by examiner

DEVICES, SYSTEMS AND METHODS FOR TREATING BACK PAIN WITH EMS

CROSS-REFERENCE TO RELATED APPLICATION

This application is a national phase filing under 35 U.S.C. § 371 of International Application No. PCT/US2020/047337, filed Dec. 21, 2020, which claims priority to and the benefit of U.S. Application No. 62/891,012, filed Aug. 23, 2019. Each of these applications is incorporated herein by reference in its entirety.

FIELD

This application relates generally to devices, systems, and methods for treating lower back pain. Optionally, the devices, systems, and methods can use electromagnetic stimulation to treat lower back pain.

BACKGROUND

Chronic lower back pain (LBP) is one of the main causes of disability affecting the general population. About 80% of adults experience LBP at some point in their lifetime. Nearly 90% of patients with LBP are considered as having nonspecific LBP (NS-LBP), since the cause of back pain is unknown. Opioids are the most common prescription drugs for US adults with LBP. Alternative treatments with mixed and unsatisfactory results include acupuncture, physical therapy, and surgery. Accordingly, a non-invasive, drug-free alternative is desirable.

SUMMARY

Described herein, in one aspect, is a method for treating lower back pain in a patient. The method can comprise positioning an electromagnetic stimulation coil at a location sufficient to deliver electromagnetic stimulation to a spine of the patient. The electromagnetic stimulation coil can be used to provide electromagnetic stimulation to the spine of the patient.

In another aspect, a device for treating lower back pain in a patient can comprise a seat portion and a backrest portion coupled to the seat portion. An electromagnetic stimulation coil can be operatively associated with the backrest portion. The electromagnetic stimulation coil can be positioned to apply electromagnetic stimulation to a spine of the patient while the patient is seated on the seat portion.

In another aspect, a system can comprise the device for treating lower back pain in a patient. At least one electrode can be configured to measure a CMAP response in a muscle of a patient sitting on the seat portion of the device. A processor can be configured to receive a signal from the least one electrode that is indicative of the CMAP response in the muscle of the patient. A display can be communicatively coupled to the processor. The processor can be configured to cause the display to display information corresponding to the CMAP response in the muscle of the patient. A position of the electromagnetic stimulation coil of the device relative to the backrest portion of the device can be adjustable based on the displayed information.

Additional advantages of the invention will be set forth in part in the description that follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

These and other aspects of the invention will become more apparent in the detailed description in which reference is made to the appended drawings wherein.

DETAILED DESCRIPTION

Figure 1:
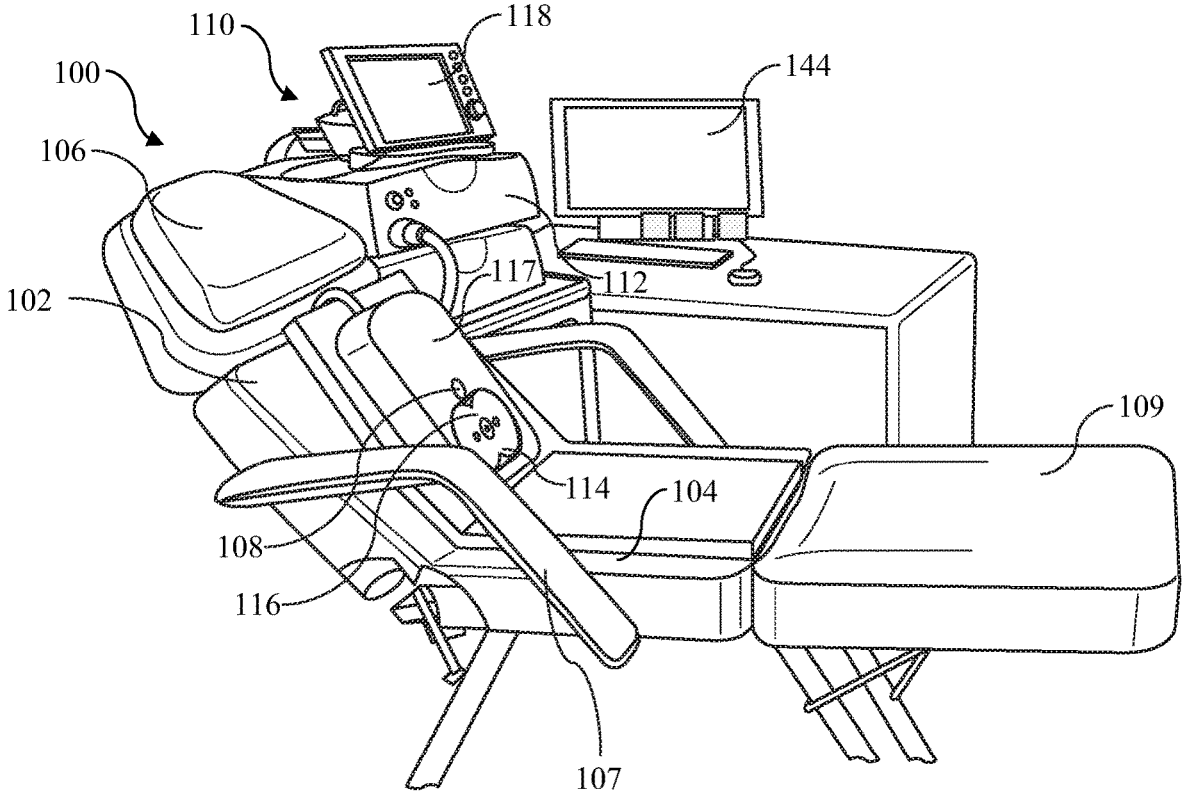
FIG. 1 is a perspective view of an exemplary chair having an embedded electromagnetic coil, in accordance with embodiments disclosed herein.

The present invention can be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, and, as such, can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "a session" can include two or more such sessions unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Optionally, in some aspects, when values are approximated by use of the antecedent "about," "approximately," "generally," or "substantially," it is contemplated that values within up to 15%, up to 10%, up to 5%, or up to 1% (above or below) of the particularly stated value or characteristic can be included within the scope of those aspects.

As used herein, the terms "optional" or "optionally" mean that the subsequently described event or circumstance may or may not occur, and that the description includes instances where said event or circumstance occurs and instances where it does not.

The word "or" as used herein means any one member of a particular list and also includes any combination of members of that list.

The lumbosacral spine comprises the five lumbar vertebral bones (L1-L5, with L1 being the upper-most vertebral bone of the group), the sacrum, and the coccyx. The sacral base, S1, is the upper and wider end of the triangular-shaped sacrum. S1 comprises a body on the top with wing-shaped bones on either side, called the alae. L5 and S1 are joined by the lumbosacral facet joints lined with articular cartilage. Electromagnetic stimulation (EMS) can be applied at a lumbosacral level for pain reduction in patients suffering from LBP. The spinal cord EMS can use electromagnetic induction of an electric field through intact tissue to underlying structures. Repetitive EMS applied at a cranial level (e.g., transcranial magnetic stimulation, (TMS)) can alter excitability at cortico-motor circuitry and currently is an FDA approved treatment for drug resistant depression. As is known in the art, the H-reflex (also known as "Hoffman's Reflex") of a muscle can be measured using an H-reflex test that is performed using an electric stimulator, which typically provides current of short duration and small amplitude, and an electromyography (EMG) set, which records the muscle response. Low frequency (e.g., about 0.2 Hz) EMS over the spinal cord can induce neuromodulation of H-reflex responses (i.e., decrease in threshold intensity and facilitation of H-responses) in chronic spinal cord injured rats. Low frequency (e.g., about 0.2 Hz) EMS applied at L4-S1 spinal levels can induce similar neuromodulation of H-reflex responses (i.e., leftward shift in threshold intensity and facilitation of H-responses). In animal models, in contrast with low frequency EMS, administration of high frequency (e.g., about 20 Hz) EMS can induce significant reduction of H-reflex amplitude and a rightward shift of threshold intensities. In some aspects, a patient can receive up to ten sessions of EMS. Pain can be evaluated before and after each session using a visual analog scale (VAS) as is known in the art. Immediate, significant pain reduction can be shown after each session. Moreover, prolonged administration of EMS can result in overall sustained pain relief. Accordingly, spinal EMS can serve as an effective, non-invasive treatment approach for chronic low back pain. Further, it is contemplated that, unlike conventional drug treatments that are limited, often by regulation, for patient health, spinal EMS can be provided without limitation to the number of sessions. Thus, spinal EMS can be used as a safe and effective long-term treatment.

In various aspects, EMS can be administered at a frequency of about 20 Hz, about 18 Hz, about 16 Hz, about 14 Hz, about 12 Hz, or about 10 Hz. For example, EMS can be administered at a frequency of between 18 Hz and 20 Hz, between 16 Hz and 18 Hz, between 14 Hz and 16 Hz, between 12 Hz and 14 Hz, between 10 Hz and 12 Hz, or below 10 Hz. In further aspects, EMS can be administered at a frequency of about 22 Hz, about 25 Hz, about 30 Hz, about 50 Hz, or about 100 Hz or more. For example, EMS can be administered at a frequency of between 20 Hz and 22 Hz, between 22 Hz and 25 Hz, between 25 Hz and 30 Hz, between 30 Hz and 50 Hz, or between 50 and 100 Hz. A therapeutic EMS session can optionally have a duration of about twenty minutes, or about fifteen minutes, or about twelve minutes, or about ten minutes, or about nine minutes, or about eight minutes, or about five minutes. For example, optionally, the therapeutic EMS session can have a duration of between fifteen and thirty minutes. In further aspects, the session can have a duration of about twenty two minutes, about twenty-five minutes, about thirty minutes, or about an hour or more. Each session can comprise a series of stimulation spans (during which stimulation is applied) and a series of breaks in between each stimulation span (during which no stimulation is applied). The breaks' duration can be selected to be sufficient to provide patient comfort as well as sufficient for the muscles and cell polarity to normalize/recover so as not to cause excessive impedance to the energy wave form from each successive/subsequent impulse. For example, each stimulation span can have a duration of about two, about three, about five, about eight, about ten, or more seconds of stimulation. For example, the stimulation span can be between three and ten seconds of stimulation. Each break can be about five seconds, ten seconds, fifteen seconds, twenty seconds, twenty five seconds, thirty seconds, or a minute. For example, the break can be between five seconds and a minute, or, optionally, between ten seconds and thirty seconds. In further aspects, a session can exclude breaks and comprise one long stimulation span. A treatment can include at least one session, or, optionally, a plurality of sessions (e.g. two, three, five, ten, fifteen, or twenty or more). Sessions can be performed twice per week, or once per week, or several times or more per week. Optionally, it is contemplated that the pulse frequency can vary within a session and/or from one session to another session. In exemplary aspects, each session can comprise 4000 pulses comprising 5 seconds of stimulation (i.e., 5-second spans of stimulation) administered at about 20 Hz with twenty-five second breaks in between. As can be appreciated, neuromodulation can involve specific parameters and frequencies to induce inhibition or excitation on a cellular level for a particular subject. The exemplary parameters disclosed herein have been shown to achieve desirable effects in both human and animal subjects.

Electrodes such as, for example, wireless electrodes, can be positioned on the patient's leg for measuring EMS-evoked responses and to record electrically evoked M-wave and H-reflex values. Although specific frequencies and durations are disclosed herein, it is contemplated that the disclosed devices, systems, and methods permit the use of any effective frequency, for any effective session duration, and for any effective stimulation span duration. The EMS intensity can be selected as 110-150% (e.g., optionally 120%) of a minimum intensity to evoke Soleus compound muscle action potential (CMAP) response. In further aspects, it is contemplated that EMS intensity can be determined as a function of the intensity required to evoke contraction of the multifidus (MF) muscles, wherein observation of lumbar spine extension can indicate contraction of the multifidus muscles. For example, the intensity can be between 110-150% (e.g., optionally 120%) of the intensity required to evoke contraction of the MF muscles. It is contemplated that this intensity determination method can be preferable for clinicians that do not have sufficient expertise to measure CMAP response. In exemplary aspects, it is contemplated that the minimum intensity for evoking contraction and the preferred stimulation intensity can be determined manually by a clinician or other health care worker. Alternatively, in other exemplary aspects, it is contemplated that one or more of these intensities can be determined in an automated fashion using at least computing device as further disclosed herein. As one example, a clinician can provide an input to a computing device that is indicative of contraction, and a processor of the computing device can then determine the preferred stimulation intensity. In further aspects, it is contemplated that the processor of the computing device can be configured to instruct the device to provide stimulation at the preferred stimulation intensity.

Figure 2:
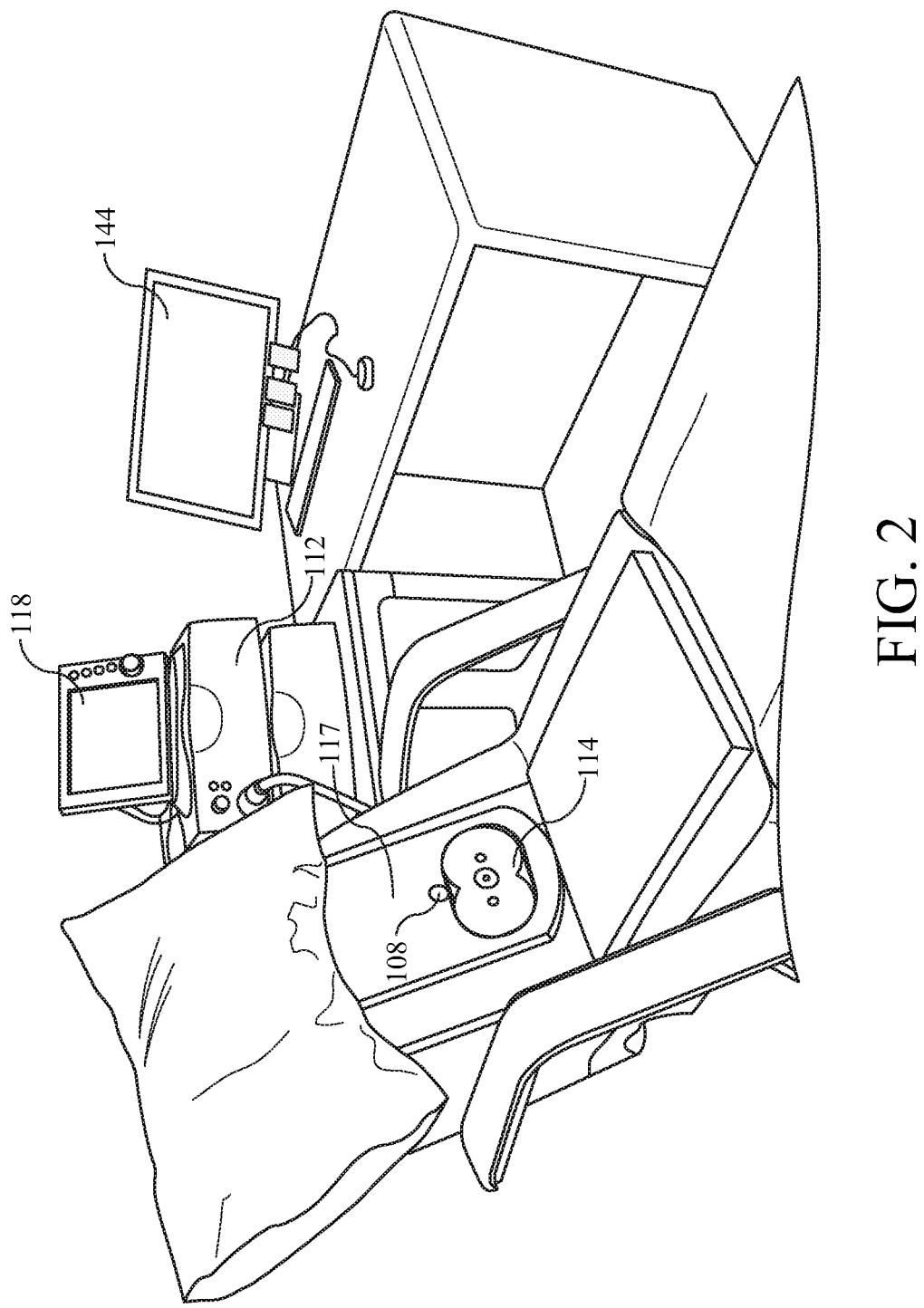
FIG. 2 is another perspective view of the chair as in FIG. 1.
Figure 3:
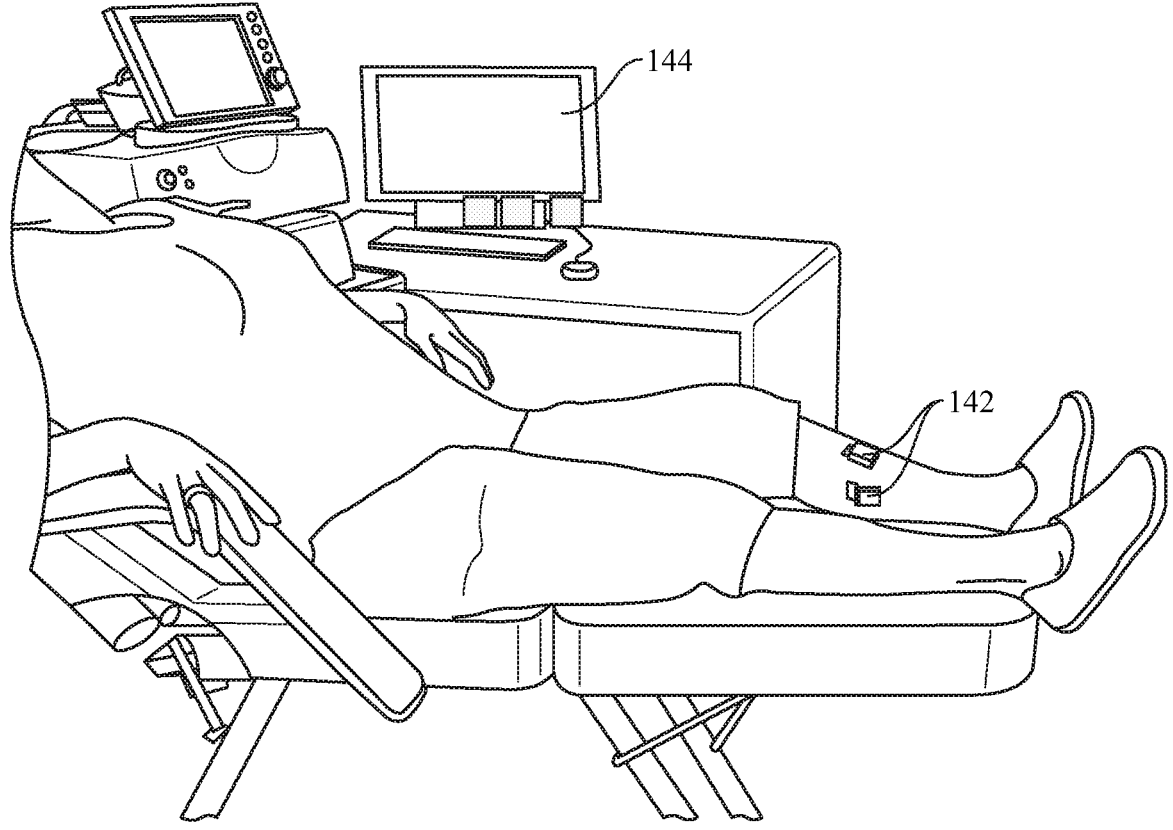
FIG. 3 is a perspective view representing a person's position in the chair of FIG. 1.

Referring to FIGS. 1-3, according to various aspects, EMS in accordance with methods disclosed herein can be administered via a chair or other patient support structure (e.g., a bed) having an embedded or attached electromagnetic stimulation device 110. Although the following embodiments describe the patient support structure as a chair, it is contemplated that the electromagnetic stimulation (EMS) device 110 can be embedded or attached to mattresses, beds, exam tables, and other patient support structures in the same or an analogous manner.

The chair 100 can comprise a seat portion 104 and a backrest portion 102. A headrest 106 can extend from the backrest portion 102. The headrest 106 can include additional padding and can have a selected (optionally, adjustable) angular orientation with respect to the backrest portion's general direction of extension (e.g., a longitudinal axis of the backrest portion 102). The chair 100 can further be fitted with various pillows for providing patient comfort.

Figures 4A, 4B:
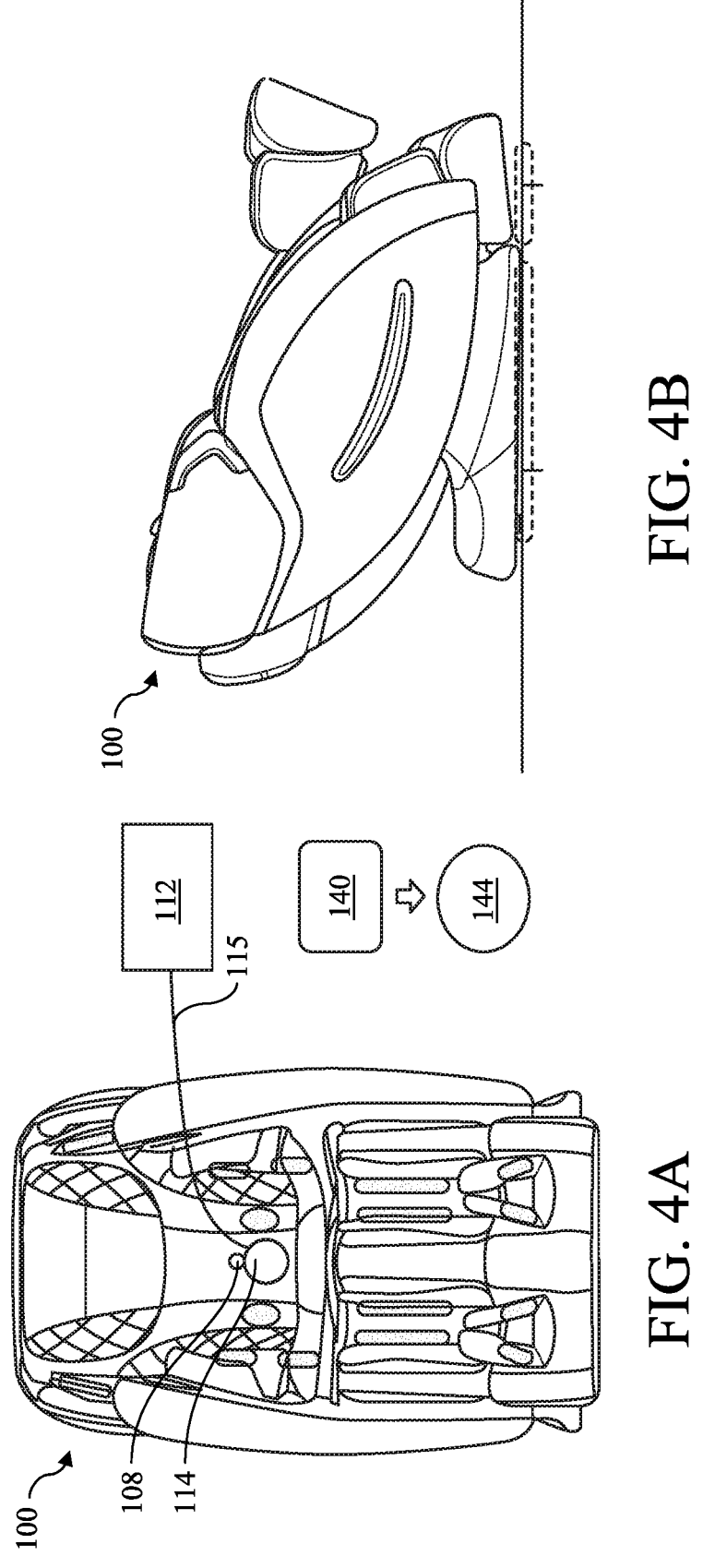
FIG. 4A is a front view of an exemplary chair in accordance with embodiments disclosed herein.
FIG. 4B is a side view of the chair of FIG. 4A, shown in a reclined configuration overlaid with a non-reclined configuration, in accordance with embodiments disclosed herein.
Figure 9:
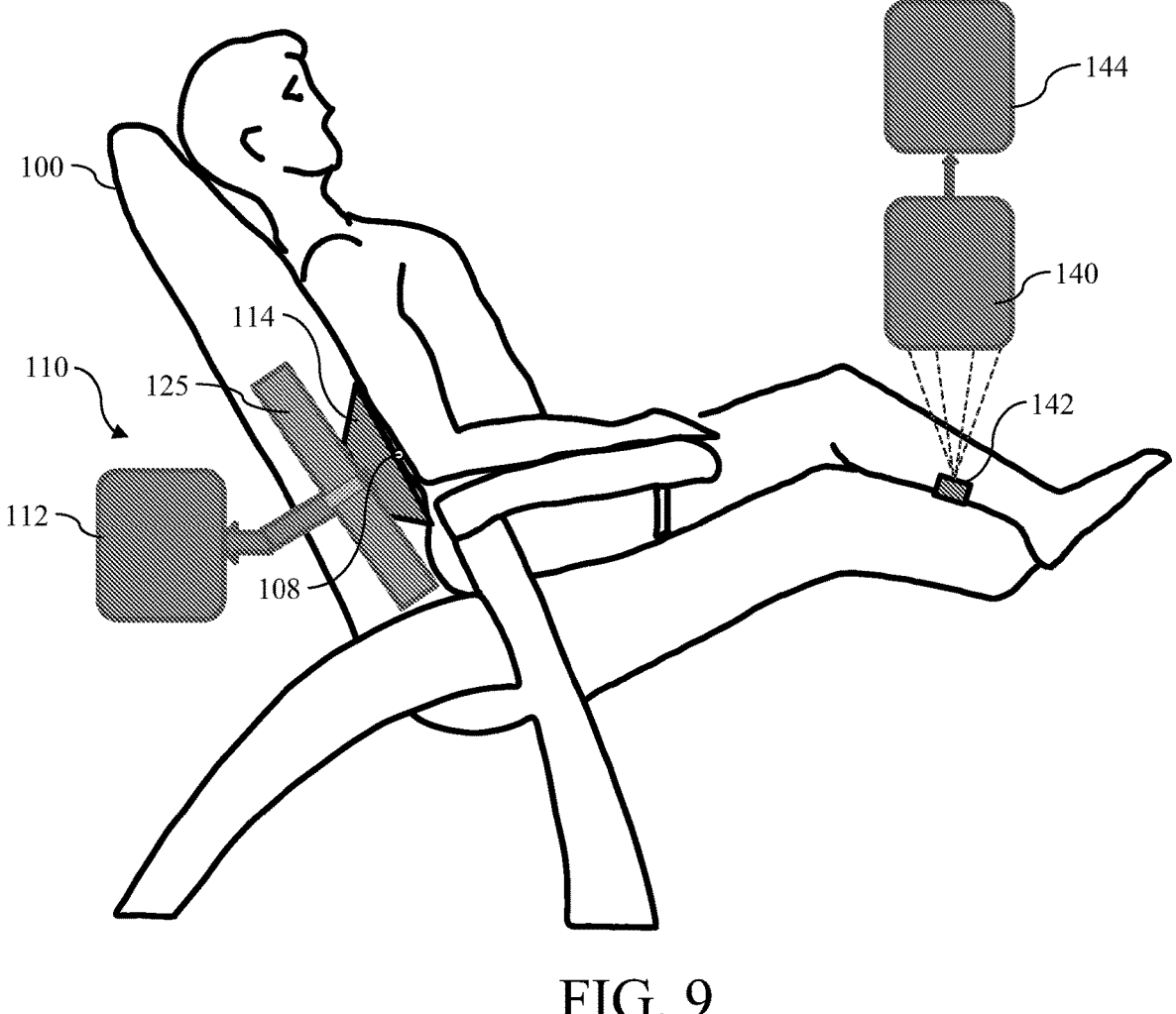
FIG. 9 illustrates a schematic of a system for providing EMS in accordance with embodiments disclosed herein.

The chair 100 can optionally be selectively and adjustably pivotable (i.e., reclinable) so that the backrest portion 102 can be positioned at a selected angle with respect to the seat portion 104. Optionally, backrest portion 102 of the chair can pivot from about and between a starting angular position to a fully reclined position. For example, the backrest portion 102 can pivot from a ninety degree or substantially vertical angle to flat (i.e., 180 degrees or at a substantially horizontal angle), wherein the seat portion 104 is parallel to, or substantially parallel to, the backrest portion 102. Similarly, the seat portion 104 can optionally be pivotable to a select angle with respect to the ground. The backrest portion 102 of the chair and, optionally, the seat portion 104 can be set at select angles at which the patient's weight applies force to the backrest portion at a desired distribution or location. Controls for setting the angular orientation of the backrest portion (e.g., a wireless remote controller) can be positioned away from the chair or can be configured to be temporarily disabled so that the patient cannot move the chair angle after a coil of the EMS device 110 has been properly positioned as further disclosed herein. Optionally, such controls can be provided in the form of a remote computing device (i.e., a smartphone, tablet, laptop computer, and the like) that is communicatively coupled to a mechanical actuator that is configured to effect selective pivotal motion of the backrest. The chair can comprise elastic foam or other materials for providing comfort to the patient. Optionally, the chair 100 can comprise armrests 107 and/or leg supports 109 that support the patient's legs in a horizontal position. It is contemplated that the chair can be positioned based on patient comfort, preference, or clinical needs. It is contemplated that the recumbent position as shown in FIG. 4B can optionally be preferable for patient comfort. FIG. 9 illustrates perspective views of a chair 100 that is movably supported on wheels. The chair 100 can comprise a deployable footrest 166 that can be movable from a stowed position, in which the footrest is beneath the chair, and a use position, in which the footrest extends forwardly from the chair.

Referring to FIGS. 1, 4A, 4B, and 9, the EMS device 110 can comprise a current generator 112 and an electromagnetic coil 114 (referred to herein also an as EMS coil). Such EMS coils are commercially available and can be configured or controlled to provide maximum power, optimal focality, and other desired properties and parameters for providing stimulation to the subject. The current generator 112 can be in electrical communication with the electromagnetic coil 114 via a cable 115 or wire (optionally, a plurality of cables or wires). The electromagnetic coil 114 can optionally be disposed within a housing 116, which can be operatively associated with, coupled to, or at least partially embedded within the backrest portion of the chair. In other embodiments, instead of being embedded within the chair, it is contemplated that the housing 116 (and the coil 114) can be embedded within a mattress or exam table at a location that will underlie at least a portion of the spine of a patient who is positioned on the mattress or exam table. The current generator 114 can comprise or couple to an interface 118 that enables a clinician to view and control various features, such as, for example and without limitation, frequency selection, intensity selection, stimulation span, and break duration. In some aspects, the interface 118 can comprise a processor, an input device, and a display device. Optionally, the input device and display device can cooperatively be embodied as a single structure, such as a touchscreen, tablet, or smartphone device. In some optional aspects, the interface 118 can optionally be embodied as a desktop computer, tablet, or smartphone. In further optional aspects, the interface 118 can be embodied as a special-purpose computer. For example, many commercially available EMS devices comprise a built-in interface for providing manual control over the stimulation parameters as a stand-alone device. Such a commercially available EMS device can be adapted for use with the chair 100. The EMS device 110 can optionally be a conventional EMS device, such as, for example, a MAG-STIM SUPERRAPID stimulator (MAGSTIM Inc., Eden Prairie, MN). The EMS device 110 can have a safety shut-off feature that measures coil temperature and shuts off the coil when the coil temperature reaches a threshold. For example, the threshold temperature can optionally be between 35 and 45 degrees Celsius (e.g., 40 degrees Celsius).

The electromagnetic coil 114 can be positioned in, or extend at least partially from, the backrest portion of the chair (or the upper surface of a mattress or table). For example, as shown in FIG. 1, the electromagnetic coil can be positioned in a foam casing 117 that is placed on (optionally, secured to) the chair (or mattress or exam table). The electromagnetic coil can be in a foam casing so that the electromagnetic coil can be flush or substantially flush with the patient's back when the patient rests against and compresses the foam casing in order to deliver the most focused and effective electromagnetic pulse to the underlying tissue of the patient's back. In further embodiments, the chair's backrest cushions can have recesses that receive the electromagnetic coil, with the electromagnetic coil being flush or substantially flush with the patient's back when the patient rests against the backrest cushions.

Figure 6:
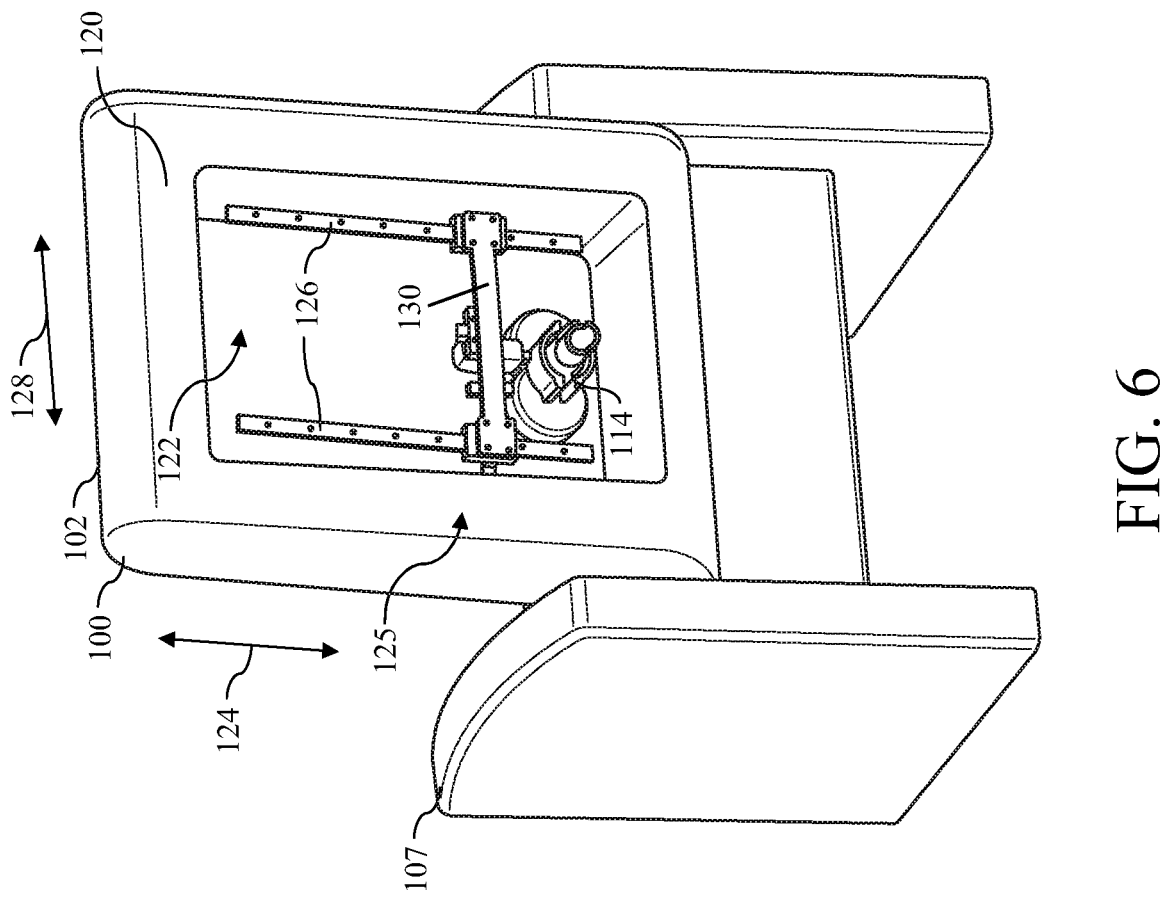
FIG. 6 is a rear view of an exemplary chair having an electromagnetic coil inset within the back side of the chair.
Figure 8:
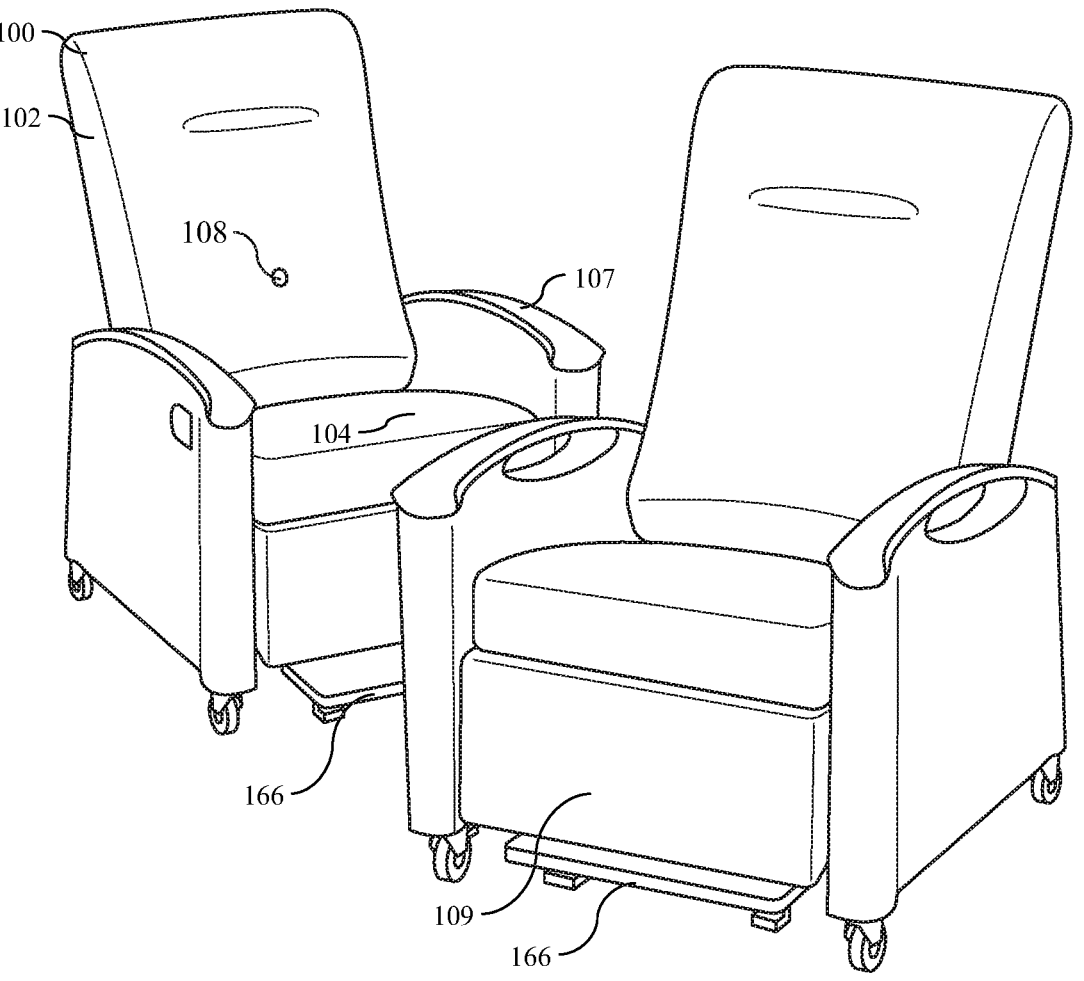
FIG. 8 includes front perspective views of an exemplary chair having an electromagnetic coil inset therein.

Referring to FIG. 6, in further aspects, the electromagnetic coil 114 can optionally be positioned on a rear side 120 of the backrest portion 102 of the chair 100 (or on a bottom side of a mattress or exam table). For example, the rear side 120 of the backrest portion can define a recess 122 within which the electromagnetic coil 114 can be positioned. It can be desirable to have minimal (e.g., less than ½ inch, or less than ⅛ inch thick) material or, optionally, no material disposed between the electromagnetic coil 114 and the patient's back.

The electromagnetic coil 114 can be set in a location that is configured to position the electromagnetic coil within a selected area of stimulation of the patient's spinal cord (e.g., near L4-S1 vertebrae). Optionally, the position of the coil can be adjustable so that the coil can be moved along a first (longitudinal) axis 124 of the backrest portion 102 of the chair 100 (or a longitudinal axis of a mattress or exam table) to be positioned at different positions relative to the back of a patient (to address changes in the desired focal area to be stimulated), or to accommodate variations in patient height (or other patient characteristics). Optionally, the electromagnetic coil can be selectively positioned via hook and loop fasteners (e.g., on a back side of the coil's housing opposite the patient side), a pressure sensitive adhesive, adjustable straps, combinations thereof, or various other means. In further embodiments, a clinician can position the electromagnetic coil between the chair and the patient, and the weight of the patient resting against the electromagnetic coil can hold the coil in place.

In further aspects, the position of the electromagnetic coil 114 can be adjusted via a positioning assembly 125. The positioning assembly 125 can comprise one or, optionally, and as shown, a pair of longitudinal rails 126, which extend relative to the first axis 124. In these aspects, the electromagnetic coil 114 can couple to the rail(s) 126 at a select position along the longitudinal rail(s). In further optional aspects, the electromagnetic coil can be movable relative to a second axis 128 that is perpendicular to the first axis 124. For example, the electromagnetic coil 114 can optionally couple to the longitudinal rail(s) 126 via a transverse rail 130 at a select position along the transverse rail. The position of the couplings between the electromagnetic coil 114 and the transverse rail 130, and the position of the couplings between the transverse rail 130 and the longitudinal rail(s) 126 can be selected by releasing at least one releasable fastener and then reengaging the releasable fastener(s) when the desired position is achieved. Such releasable fasteners can include clamps, locking pins, hook and loop fasteners, screws, and the like.

Referring to FIG. 2, a load sensor 108 can be disposed in the backrest portion for measuring the force that the patient's weight applies to the backrest. The load sensor can optionally be positioned near an electromagnetic coil of the EMS device as further disclosed herein. In further aspects, the load sensor can be positioned on the electromagnetic coil of the EMS device. It is contemplated that the angle of the chair can affect the pressure applied to the load sensor. The load sensor can measure the amount of force applied to the coil. With this information, the force applied to the patient can be standardized and optimized between treatment sessions to quantify the optimal therapeutic value. This can individualize the treatment for each patient since some patients may benefit from different force pressures exerted to achieve the optimal clinical benefit. The force can also be standardized between the medical professionals applying the treatments, which can be beneficial in comparison to hand-held or manually applied devices that rely on manually applied pressure that can vary based on a number of factors (e.g., variance between different professionals applying the pressure). The pressure can optionally be measured in pounds per square inch. Optionally, a minimum pressure or force applied to derive therapeutic benefit can be an initial metric for the therapy with subsequent increases in pressure if needed or desired. The load sensor can optionally be selectively positioned with respect to the chair to accommodate variability in body morphology among patients that impact the body surface area that is in direct contact with the load sensor and coil. For instance, a patient with a flat lumbar spine morphology (e.g., as shown in FIG. 9) can have more body surface area in contact with or more force applied to the load sensor (and, optionally, the EMS coil) as compared to a patient that has a hyper lordotic lumbar spine morphology. Standardizing both the EMS applied and the amount of force applied can enable optimizing therapeutic effects, and the results and treatment sessions can be quantified based on these settings that would be recorded in the patient's medical record. The load cell data can be provided to a computing device (e.g., a laptop, desktop, smartphone, or tablet). The computing device can be hardwired (e.g., via USB cable) to the load sensor or wirelessly connected (e.g., via Wi-Fi or Bluetooth protocols). The amount of pressure (or force) applied can optionally be stored for each patient for each session. Further, for a given patient, the computing device can provide a recommended pressure (e.g., based on force applied to other patients or based on a force applied to the same patient during a previous session and its therapeutic effect). Optionally, the computing device that is in communication with the load cell can be the same computing device that is communicatively coupled to electrodes 142 to record and analyze the neurophysiological responses from a patient or subject and/or adjust stimulation parameters of the device as further disclosed herein.

It is contemplated that certain components of the disclosed devices and systems can be modular so that they can be easily interchangeable (i.e., removable and replaceable). For example, the electromagnetic coil or EMS device can be removed, and a replacement coil can be installed in its place. Optionally, it is contemplated that the replacement coil can have different properties than the coil that was originally associated with the EMS device.

Referring to FIGS. 4A, 4B, and 9, in one exemplary embodiment, the chair 100 can have an EMS coil 114 in an adjustable position to stimulate a lumbar area of a patient. The EMS coil 114 can be in communication with an EMS stimulator 112. The EMS stimulator 112 can be remote from the chair 100 and can connect via an electrical cable. An amplifier 140 can measure neurophysiological responses (EMS-evoked EMG-responses as well as H-reflex) from the patient's leg muscles using electrodes 142 (e.g., wireless electrodes) placed on the patient's skin. A processing unit 144 in communication with the amplifier 140 can record and analyze the neurophysiological responses received from the electrodes 142. It is contemplated that the processing unit 144 can be any computing device, including for example and without limitation, a smartphone, a tablet, a laptop computer, a desktop computer, a Cloud-based computer or network, and the like. It is further contemplated that the processing unit 144 can comprise a processor and a memory that is in communication with the processor and configured to execute instructions that permit analysis and output (optionally, display) of information related to the neurophysiological responses provided by the patient. Such information can include metrics based on traces of H-reflex. For example, H-reflex traces taken before and after EMS treatment can be compared, and the differences can indicate whether the EMS parameters are optimal or if one or more parameters should be changed. Optionally, such an analysis can be automated. Optionally, such analyses can be done at one or more initial sessions and then only as needed thereafter. EMS parameters (e.g., intensity and/or session duration) can optionally be increased based on changes in H-reflex traces, other captured data, or patient feedback (e.g., VAS data). Optionally, the captured data (e.g., neurophysiological responses) can be analyzed and displayed on a single computing device (e.g., a desktop computer, tablet, smartphone, etc.). In further aspects, the data capture (and, optionally, processing) can be performed on a first computing device, and a second (remote) computing device can display the data. For example, the first computing device can be configured to capture and record data, as well as, optionally, process the data, and the second computing device (that can be visible to a clinician) can receive the data from the first computing device and display the data. In further aspects, the second computing device can perform some or all of the processing of the data. Optionally, one or both of the first and second computing devices can be a cloud computing device. In further aspects, it is contemplated that the processing unit 144 can be omitted.

Figure 5:
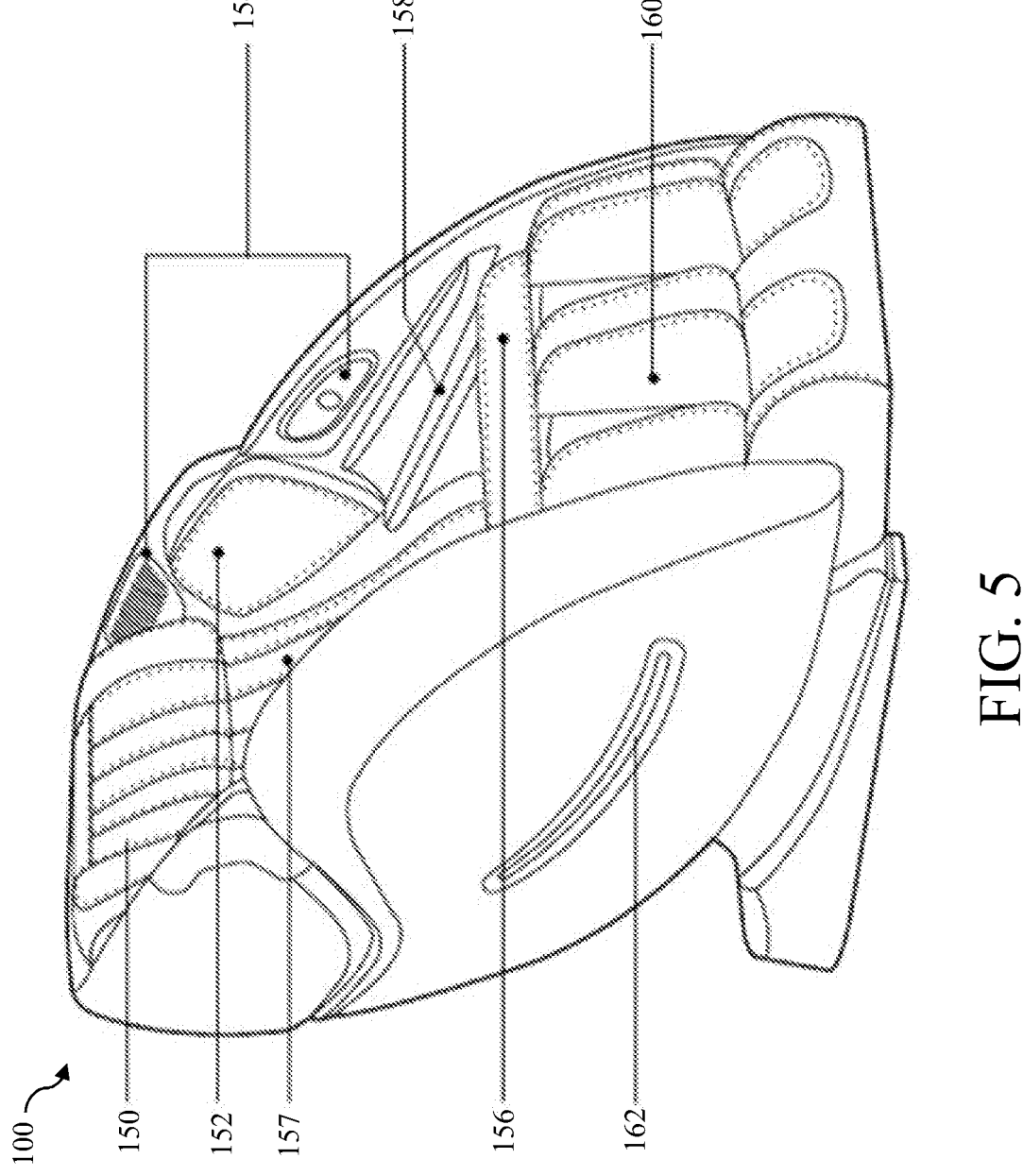
FIG. 5 is a perspective view of the chair of FIG. 4A in accordance with embodiments disclosed herein.
Figure 7:
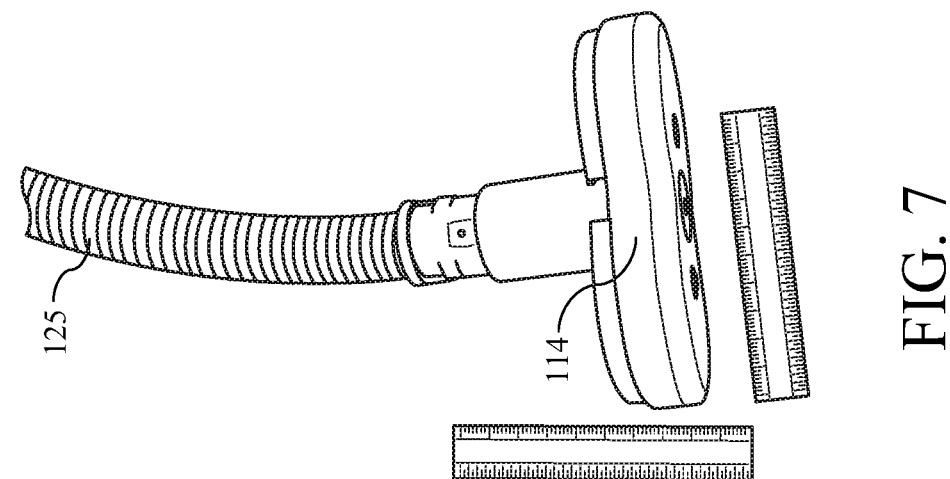
FIG. 7 is a top view of the electromagnetic coil of FIG. 6 beside six-inch rulers for size comparison.

Referring to FIG. 5, in some optional embodiments, the chair 100 can comprise cervical orthopedic anatomical support pillows 150 and side comfort pillows 152. Speakers 154 (e.g., Bluetooth speakers) can be used for communicating with the patient and/or to play relaxing music. Recumbent supportive orthopedic anatomical support pillows 156 can house the EMS coil 114. The chair 100 can comprise armrests 107. The armrests 107 can optionally have a straight profile (FIG. 5) or an arcuate profile (FIG. 9). A seat pan 158 can have supportive tilt. The chair 100 can comprise lower extremity neutral support pillows 160. Optionally, a lever 162 can enable reclined angle control. The chair 100 can optionally have three discrete recumbent positions (e.g., substantially vertical, substantially horizontal, and an intermediate position); however, it is contemplated that any number of discrete recumbent positions can be used.

In addition to the patient support structure being embodied as a chair, it is contemplated that the electromagnetic stimulation (EMS) device 110 can be embedded or attached to mattresses, beds, exam tables, and other patient support structures in the same or an analogous manner. For example, the support structure (e.g., mattress, bed, table, etc.) can define an upper patient support surface that can be flat or contoured to match the curvature of a patient's back (and, optionally, head, neck, buttocks, and legs). The upper patient support surface can optionally be defined by a single body (as opposed to a backrest portion that is coupled to a seat portion. The upper patient support surface can be rigid or compressible (e.g., supported by foam). The electromagnetic coil 114 of the EMS device 100 can be at least partially embedded within the support structure. For example, the upper patient support surface can define a recess that can at least partially receive the electromagnetic coil 114. In further aspects, the electromagnetic coil 114 can be positioned beneath the upper patient support surface. In still further aspects, the electromagnetic coil 114 can be positioned on top of the patient support surface. The support structure can have a longitudinal dimension and a transverse dimension, and the electromagnetic coil 114 can be positioned with respect to the longitudinal dimension of the support structure so that the electromagnetic coil 114 can be optimally positioned to provide EMS to a patient positioned (e.g., lying) on the support structure. For example, optionally, the electromagnetic coil 114 can optionally be positioned in the middle of the support structure with respect to both the longitudinal and transverse dimensions. In further aspects, the electromagnetic coil 114 can be offset from the middle of the support structure relative to the longitudinal dimension. Optionally, some or all of the support structure can be selectively pivoted with respect to a horizontal plane. In still further aspects, the support structure can be configured to support the patient lying on his/her side. For example, the support structure can have padding that support the side profile of the patient so that the patient's spine remains straight. The electromagnetic coil 114 can be selectively positioned (optionally, on an adjustable positioning assembly) to provide lower-back EMS.

Various features of the disclosed devices, systems, and methods are designed to achieve safe treatment for lower back pain. The treatment can be standardized to optimize effectiveness based on measured results and outcomes. For example, feedback from the electrodes 142 on the patients' legs or patient VAS feedback can enable clinicians to adjust stimulation timing, frequency, intensity, focal point/area location, etc. Using such feedback, settings for the optimal position (e.g., position of the EMS coil 114 with respect to the patient's back and the angle of recline of the backrest 102) and EMS settings can be tailored for each patient or standardized across multiple patients. The settings can be documented and repeatable for subsequent procedures. The device can be configured for hands-free operation. For example, a clinician can set up and begin the treatment, and the treatment can continue and end without further input. Thus, it is contemplated that the clinician can leave the patient during the duration of treatment. Because the treatment is non-invasive, the patient can nap, relax, listen to music, or watch TV as the treatment is being performed. The patient is not required to remain NPO (without food and fluids) prior to treatment. No recovery time is required post treatment, and the patient can drive home after each treatment. The device can be configured for outpatient procedures and can be safe across all adult age ranges. The EMS treatment can be coupled with other treatment modalities (e.g., physical, occupational and aquatic therapy, acupuncture, chiropractor, yoga, cognitive behavioral therapy, as well as trigger point injections, nerve block injections, and/or steroid injections). For example, a chronic pain patient can use a primary treatment modality supplemented or augmented by another modality such as an interventional modality including trigger point injections to address the pain aspects of their condition with periodic physical therapy should there be a functional deficit involved. Through use of the disclosed devices, systems, and methods, reliance on opioids can be reduced. Further, treatment can be automated using the devices, systems and methods disclosed herein, thereby enabling social distancing as demanded by the Covid-19 pandemic To provide the treatment, one or more recording electrodes can be positioned on one or both the legs of a patient. For example, electrodes 142 can be positioned to determine CMAP response at the Soleus, Medial Gastrocnemius (MG), and Lateral Gastrocnemius (LG), respectively. The optimal position of the EMS coil can be determined as the location at which EMS induces maximum CMAP response in the recording electrodes on any one of the leg muscles. Thus, the EMS coil 114 can be moved until it is in the optimal placement. Additionally, or alternatively, as stated herein, the EMS coil 114 can be moved until visible contraction of MF muscles and lumbar spine extension are evoked.

The intensity can be selected by determining the lowest intensity that evokes a Soleus CMAP response. As an alternative to CMAP response, the intensity could be determined based on minimum intensity required to evoke visible contraction of MF muscles and lumbar spine extension. That is, a clinician/medical professional can use either the CMAP response, as disclosed herein, or observation of MF muscle contraction and lumbar spine extension.

H-reflex can be determined by positioning a stimulation probe 143 for electric stimulation of the tibial nerve, generating stimulating signals at the stimulation probe 143, and receiving signals at the recording electrode 142 at the soleus muscle.

EXAMPLES

It is contemplated that any content described in the following examples can be used to form an aspect of the disclosed systems and methods. Although described as separate examples, it is contemplated that particular parameters or steps of one example can be combined with parameters and steps of any other examples disclosed herein to produce additional aspects of the disclosed systems and methods. Thus, except as otherwise indicated, it is contemplated that steps or features of Example 1 can be combined with steps or features of Example 2.

Example 1

Figure 10:
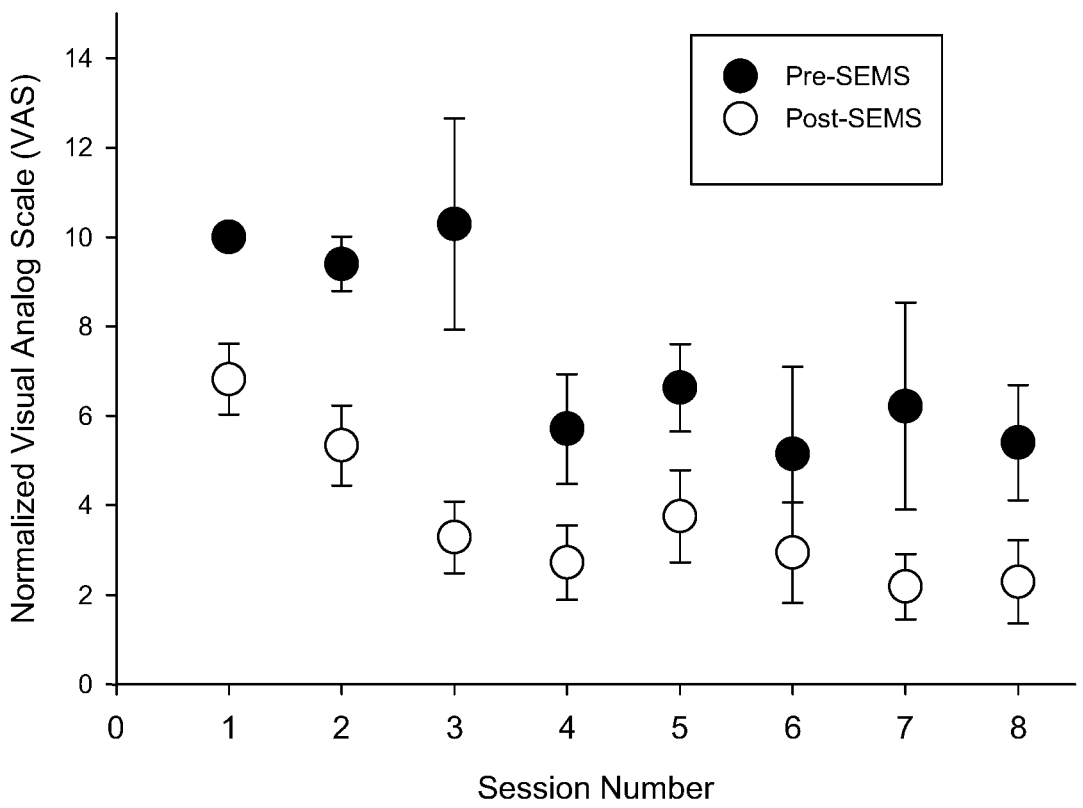
FIG. 10 is a graph showing results using methods as disclosed herein.

FIG. 10 illustrates a graph showing normalized VAS results obtained from twelve subjects before and after treatment over eight treatment sessions. Each treatment comprised 4000 pulses of 5 seconds of stimulation with 25-second breaks in between, administered at 20 Hz. Lower back pain was reduced in the sample subjects after each session, and repeated tests indicated a sustained decrease in pain. Moreover, the sample patients reported lower use of analgesics, muscle relaxants, and sleeping pills.

Example 2

In another example, thirteen patients were used as test subjects. The average age was 51+/−3.1 years; 10 were male, 3 were female; the average height was 69.6 inches+/− 1; the average weight was 227+/−17.7 lbs; the average BMI was 23+/−2; the average VAS was 4.8+/−0.48; the average ODI was 34.7+/−6.7.

The patients were screened with a questionnaire about medications and general style of life. Their vitals were determined, as well as functioning (Oswestry Disability Index, or ODI) and pain intensity according to VAS.

Figure 11:
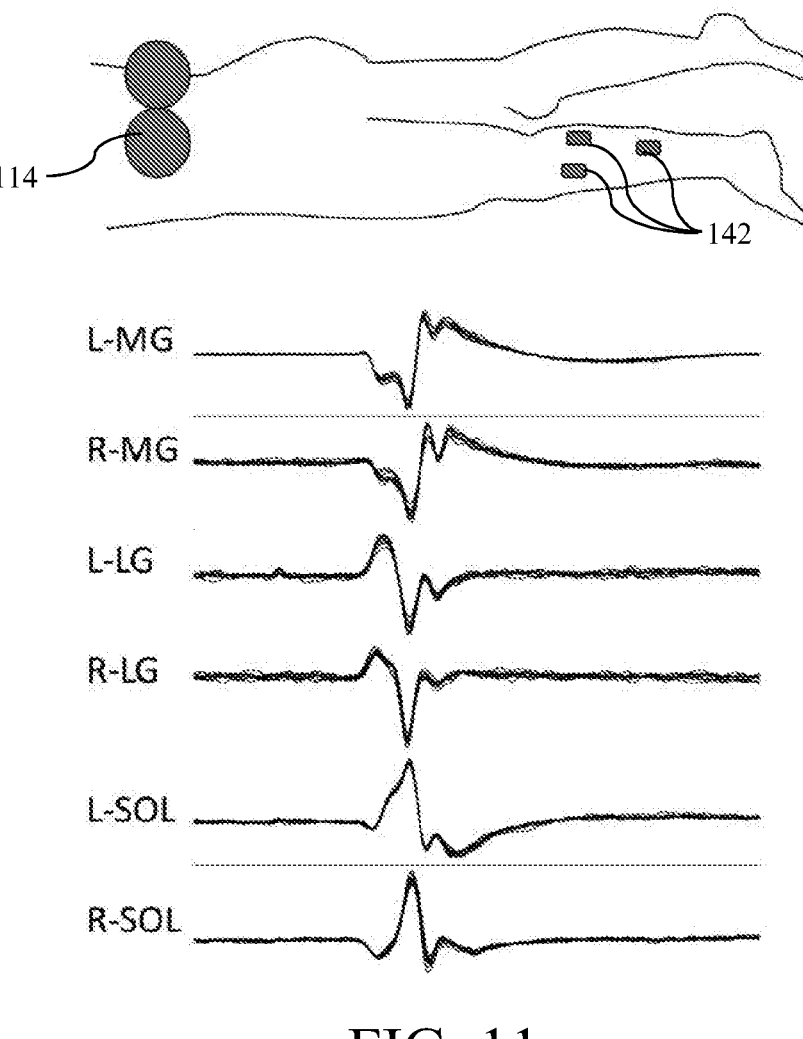
FIG. 11 illustrates exemplary electrode positions for determining CMAP response and representative signal traces of CMAP responses recorded from leg muscles and evoked by electromagnetic pulses as disclosed herein.

Referring to FIG. 11, the optimal position of the EMS coil was determined at lumbar (L1-L5) sections at which EMS induces maximum CMAP response in the leg muscles (Soleus, Medial Gastrocnemius (MG), and Lateral Gastrocnemius (LG)).

The threshold intensity was chosen to evoke minimal Soleus CMAP response.

Figure 12:
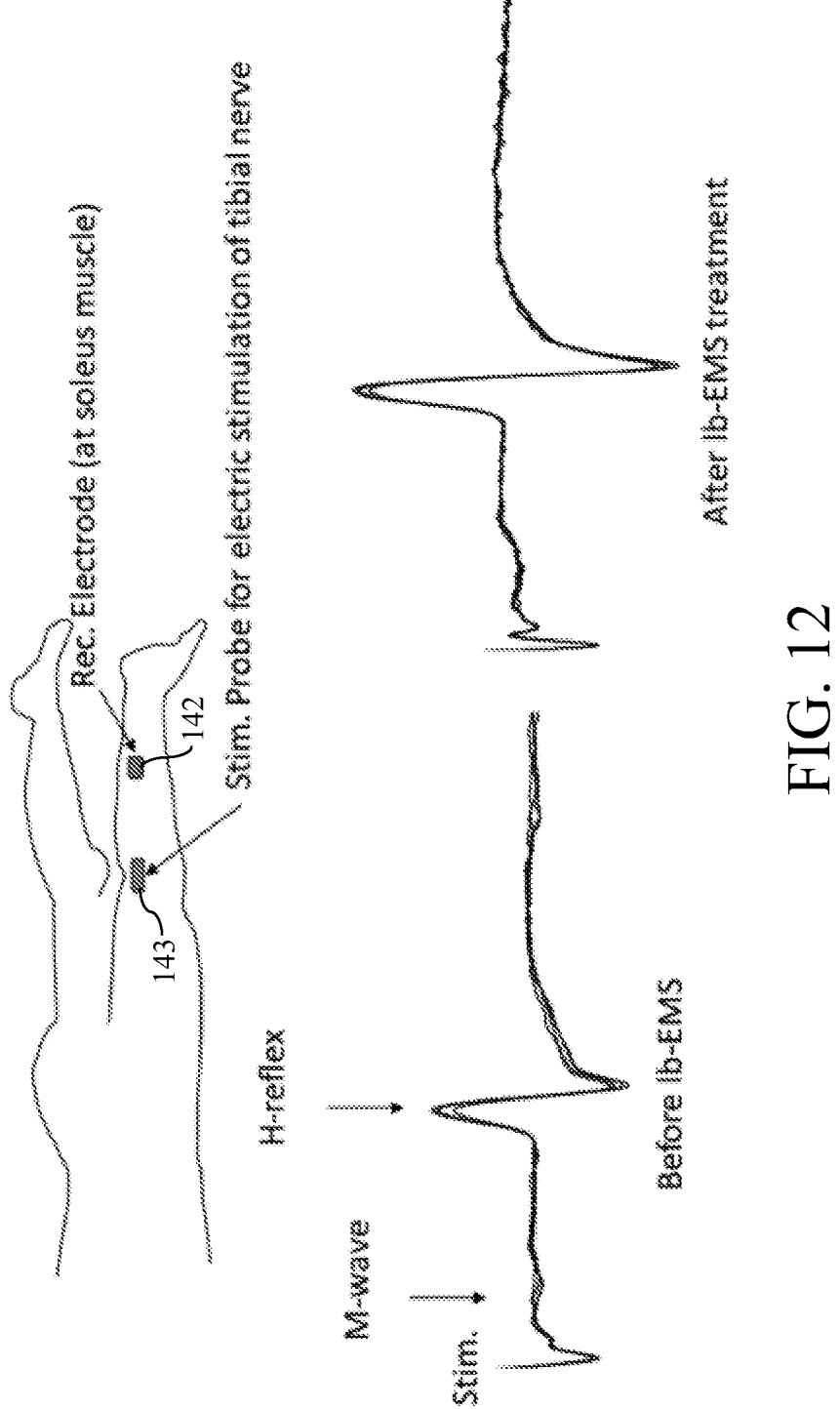
FIG. 12 illustrates exemplary electrode positions for determining H-reflex and representative signal traces of H-reflex.

Referring to FIG. 12, the H reflex was measured prior to administering EMS. EMS was then applied at 120% of Soleus CMAP threshold, the EMS comprising 4000 pulses of 5 seconds of stimulation with 25-second breaks in between, administered at 20 Hz. H reflex was then measured again to examine quantitatively how EMS affected H-reflex as a common neurophysiological measure of function at spino-muscular circuitry.

The vitals were then measured after the treatment.

Eight total sessions, 2-3 times per week over 3-4 weeks, were performed.

Figure 13:
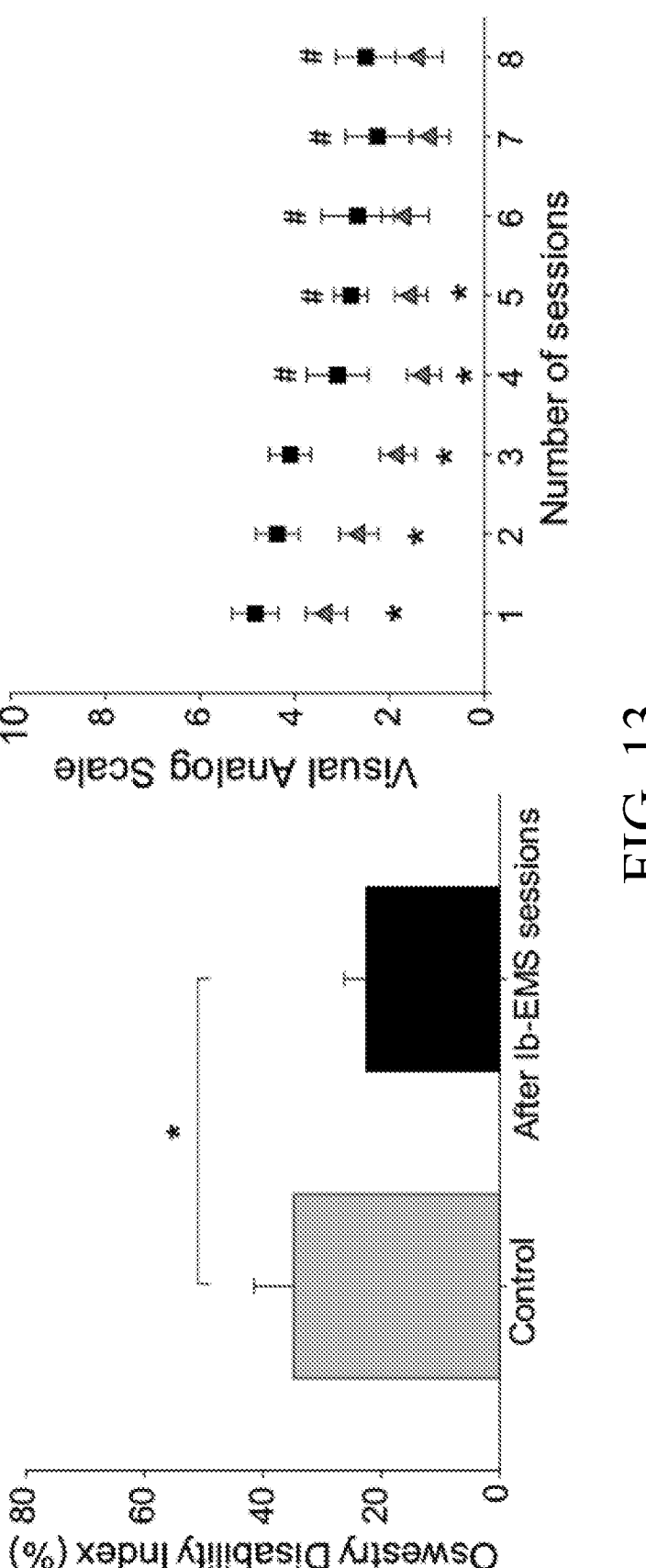
FIG. 13 is a pair of charts demonstrating pain reduction after treatment as disclosed herein.

FIG. 13 illustrates the effects of the sessions. As can be seen, the Oswestry Disability Index dropped after the series of sessions. Further, results demonstrate EMS-induced reduction of chronic LBP while comparing VAS pre- and post-administration of each session, with the reduction shown with '*'. The reduction of the level of patients" pain with increasing number of sessions is shown with '#'. Additionally, patients reported a reduction in the use of analgesics, muscle relaxants, and sleeping pills. Control studies using subthreshold intensities did not show pain reduction.

Additional devices and methods for treating spinal cords are disclosed in Hunanyan, A. S., Petrosyan, H. A., Alessi, V., & Arvanian, V. L. (2012). Repetitive spinal electromagnetic stimulation opens a window of synaptic plasticity in damaged spinal cord: role of NMDA receptors. Journal of neurophysiology, 107(11), 3027-3039. Further aspects for treating spinal cords are disclosed in Petrosyan, Hayk A., et al. "Spinal electro-magnetic stimulation combined with transgene delivery of neurotrophin NT-3 and exercise: novel combination therapy for spinal contusion injury." Journal of neurophysiology 114.5 (2015): 2923-2940. Both of the foregoing journal references are hereby incorporated by reference in their entireties.

EXEMPLARY ASPECTS

In view of the described products, systems, and methods and variations thereof, herein below are described certain more particularly described aspects of the invention. These particularly recited aspects should not however be interpreted to have any limiting effect on any different claims containing different or more general teachings described herein, or that the "particular" aspects are somehow limited in some way other than the inherent meanings of the language literally used therein.

Aspect 1: A device for treating lower back pain in a patient, the device comprising: a seat portion; a backrest portion coupled to the seat portion; and an electromagnetic stimulation coil operatively associated with the backrest portion, wherein the electromagnetic stimulation coil is positioned to apply electromagnetic stimulation to a spine of the patient while the patient is seated on the seat portion.

Aspect 2: The device of aspect 1, wherein the electromagnetic stimulation coil is disposed within a foam casing.

Aspect 3: The device of aspect 1 or aspect 2, wherein the coil is embedded within a recess in the backrest portion.

Aspect 4: The device of aspect 3, wherein backrest portion has a front surface and rear surface, wherein the recess is inset from the rear surface.

Aspect 5: The device of aspect 4, further comprising an adjustment assembly that is configured to enable selection of a position of the electromagnetic stimulation coil relative to a first axis that extends along a length of the backrest.

Aspect 6: The device of aspect 5, wherein the adjustment assembly comprises at least one longitudinal rail that extends relative to the first axis, wherein the electromagnetic stimulation coil is configured to be selectively coupled to the at least one longitudinal rail at multiple positions along the at least one longitudinal rail.

Aspect 7: The device of aspect 6, wherein the adjustment assembly is further configured to enable selection of the position of the electromagnetic stimulation coil relative to a second axis that is perpendicular to the first axis.

Aspect 8: The device of aspect 7, wherein the adjustment assembly further comprises a transverse rail that is configured to be coupled to the at least one longitudinal rail, wherein the electromagnetic stimulation coil is configured to be coupled to the transverse rail at multiple positions along the transverse rail.

Aspect 9: The device of any one of aspect 1-8, wherein the backrest portion is selectively pivotable with respect to the seat portion.

Aspect 10: The device of any one of aspect 1-8, further comprising a load sensor positioned within the backrest portion, wherein the load sensor is configured to measure a force applied to the backrest by a patient.

Aspect 11: A system comprising: the device of any one of aspect 1-8; at least one electrode configured to measure a CMAP response in a muscle of a patient sitting on the seat portion of the device; a processor configured to receive a signal from the least one electrode that is indicative of the CMAP response in the muscle of the patient; and a display that is communicatively coupled to the processor, wherein the processor is configured to cause the display to display information corresponding to the CMAP response in the muscle of the patient, wherein a position of the electromagnetic stimulation coil of the device relative to the backrest portion of the device is adjustable based on the displayed information.

Aspect 12: A method for treating lower back pain in a patient, the method comprising: positioning an electromagnetic stimulation coil at a location sufficient to deliver electromagnetic stimulation to a spine of the patient; and using the electromagnetic stimulation coil to provide electromagnetic stimulation to the spine of the patient.

Aspect 13: The method of aspect 12, wherein the electromagnetic stimulation coil is positioned to stimulate a portion of the spine of the patient between L4 and S1.

Aspect 14: The method of aspect 12 or aspect 13, further comprising: receiving one or more signals indicative of at least one compound muscle action potential (CMAP) response of the patient; adjusting a position of the electromagnetic stimulation coil based on the one or more signals.

Aspect 15: The method of aspect 14, wherein the at least one CMAP response comprises a CMAP response from each of a soleus, a medial gastrocnemius, and a lateral gastrocnemius of the patient.

Aspect 16: The method of any one of aspects 12-16, wherein the electromagnetic stimulation coil provides electromagnetic stimulation at a frequency of about 20 Hz.

Aspect 17: The method of any one of aspects 12-17, further comprising determining a threshold intensity of electromagnetic stimulation that is necessary to evoke a CMAP response of a muscle of the patient.

Aspect 18: The method of aspect 17, wherein the CMAP response is the CMAP response of a soleus of the patient.

Aspect 19: The method of aspect 17 or aspect 18, wherein using the electromagnetic stimulation coil to provide electromagnetic stimulation to the spine of the patient comprises using an electromagnetic stimulation intensity that is proportional to the threshold intensity to evoke the CMAP response of the muscle.

Aspect 20: The method of aspect 19, wherein the stimulation intensity is about 120% of the threshold intensity.

Aspect 21: The method of any one of aspects 12-20, wherein the electromagnetic stimulation coil is operatively associated with a device comprising: a seat portion; and a backrest portion, wherein the electromagnetic stimulation coil is positioned with respect to the backrest portion and provides electromagnetic stimulation to the spine of the patient while the patient is sitting on the seat portion.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

What is claimed is:

1. A device for treating lower back pain in a patient, the device comprising:

a seat portion;

a backrest portion coupled to the seat portion, wherein the backrest portion has a front surface and rear surface, wherein back portion defines a recess inset from the rear surface;

an electromagnetic stimulation coil embedded within the recess of the backrest portion, wherein the electromagnetic stimulation coil is positioned to apply electromagnetic stimulation to a spine of the patient while the patient is seated on the seat portion; and an adjustment assembly that is configured to enable selection of a position of the electromagnetic stimulation coil relative to a first axis that extends along a length of the backrest, wherein the adjustment assembly comprises at least one longitudinal rail that extends relative to the first axis, wherein the electromagnetic stimulation coil is configured to be selectively coupled to the at least one longitudinal rail at multiple positions along the at least one longitudinal rail, and wherein the adjustment assembly is further configured to enable selection of the position of the electromagnetic stimulation coil relative to a second axis that is perpendicular to the first axis.

2. The device of claim 1, wherein the electromagnetic stimulation coil is disposed within a foam casing.

3. The device of claim 1, wherein the adjustment assembly further comprises a transverse rail that is configured to be coupled to the at least one longitudinal rail, wherein the electromagnetic stimulation coil is configured to be coupled to the transverse rail at multiple positions along the transverse rail.

4. The device of claim 1, wherein the backrest portion is selectively pivotable with respect to the seat portion.

5. The device of claim 1, further comprising a load sensor positioned within the backrest portion, wherein the load sensor is configured to measure a force applied to the backrest by a patient.

6. A system comprising:
the device of claim 1;
at least one electrode configured to measure a CMAP response in a muscle of the patient sitting on the seat portion of the device;
a processor configured to receive a signal from the least one electrode that is indicative of the CMAP response in the muscle of the patient; and
a display that is communicatively coupled to the processor, wherein the processor is configured to cause the display to display information corresponding to the CMAP response in the muscle of the patient,
wherein a position of the electromagnetic stimulation coil of the device relative to the backrest portion of the device is adjustable based on the displayed information.

7. A method of using the device of claim 1 for treating lower back pain in the patient, the method comprising:

positioning the electromagnetic stimulation coil at a location sufficient to deliver electromagnetic stimulation to the spine of the patient; and
using the electromagnetic stimulation coil to provide electromagnetic stimulation to the spine of the patient.

8. The method of claim 7, wherein the electromagnetic stimulation coil is positioned to stimulate a portion of the spine of the patient between L4 and S1 vertebrae.

9. The method of claim 7, further comprising:
receiving one or more signals indicative of at least one compound muscle action potential (CMAP) response of the patient; and
adjusting a position of the electromagnetic stimulation coil based on the one or more signals.

10. The method of claim 9, wherein the at least one CMAP response comprises a CMAP response from each of a soleus, a medial gastrocnemius, and a lateral gastrocnemius of the patient.

11. The method of claim 7, wherein the electromagnetic stimulation coil provides electromagnetic stimulation at a frequency of about 20 Hz.

12. The method of claim 7, further comprising determining a threshold intensity of electromagnetic stimulation that is necessary to evoke a CMAP response of a muscle of the patient.

13. The method of claim 12, wherein the CMAP response is the CMAP response of a soleus of the patient.

14. The method of claim 12, wherein using the electromagnetic stimulation coil to provide electromagnetic stimulation to the spine of the patient comprises using an electromagnetic stimulation intensity that is proportional to the threshold intensity to evoke the CMAP response of the muscle.

15. The method of claim 14, wherein the stimulation intensity is about 120% of the threshold intensity.

\* \* \* \* \*